US008152858B2

(12) United States Patent
Fujinuma et al.

(10) Patent No.: US 8,152,858 B2
(45) Date of Patent: Apr. 10, 2012

(54) HEAD HAIR DYEING METHOD

(75) Inventors: Hiroyuki Fujinuma, Tokyo (JP); Takashi Matsuo, Tokyo (JP); Masahiko Ogawa, Tokyo (JP); Takeshi Iizaki, Tokyo (JP); Hiromi Saimiya, Tokyo (JP); Kazuhiro Okada, Tokyo (JP); Tomohito Koshika, Tokyo (JP); Makoto Iijima, Tokyo (JP); Hajime Miyabe, Tokyo (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 12/769,182

(22) Filed: Apr. 28, 2010

(65) Prior Publication Data

US 2010/0236570 A1    Sep. 23, 2010

Related U.S. Application Data

(63) Continuation-in-part of application No. 12/739,835, filed as application No. PCT/JP2007/001160 on Oct. 24, 2007, now abandoned.

(30) Foreign Application Priority Data

Aug. 21, 2009    (JP) ................................ 2009-191775

(51) Int. Cl.
    *A61Q 5/10*    (2006.01)
(52) U.S. Cl. ......... 8/405; 8/431; 8/457; 8/526; 132/202; 132/208
(58) Field of Classification Search .............. 8/405, 431, 8/457, 526; 132/202, 208
    See application file for complete search history.

(56) References Cited

U.S. PATENT DOCUMENTS

| | | | |
|---|---|---|---|
| 3,341,418 | A | 9/1967 | Moses et al. |
| 3,709,437 | A | 1/1973 | Wright |
| 4,823,985 | A | 4/1989 | Grollier et al. |
| 4,961,925 | A | 10/1990 | Tsujino et al. |
| 5,143,518 | A | 9/1992 | Madrange et al. |
| 5,848,730 | A | 12/1998 | Kawase et al. |
| 5,968,486 | A | 10/1999 | Newell et al. |
| 7,955,400 | B2 | 6/2011 | Fujinuma et al. |
| 2004/0213752 | A1* | 10/2004 | Fujinuma et al. ............ 424/70.1 |
| 2010/0126522 | A1 | 5/2010 | Fujinuma et al. |
| 2010/0126523 | A1 | 5/2010 | Fujinuma et al. |
| 2010/0236570 | A1 | 9/2010 | Fujinuma et al. |
| 2010/0242187 | A1 | 9/2010 | Miyabe |
| 2010/0251488 | A1 | 10/2010 | Fujinuma et al. |
| 2010/0257677 | A1 | 10/2010 | Miyabe et al. |
| 2010/0299848 | A1 | 12/2010 | Fujinuma et al. |
| 2010/0313905 | A1 | 12/2010 | Fujinuma et al. |
| 2010/0316583 | A1 | 12/2010 | Fujinuma et al. |
| 2011/0073128 | A1 | 3/2011 | Ogawa et al. |

FOREIGN PATENT DOCUMENTS

| | | |
|---|---|---|
| DE | 1801518 | 1/1971 |
| EP | 113418 | 7/1984 |
| EP | 0 503 507 | 9/1992 |
| EP | 1 055 425 | 11/2000 |
| EP | 0 877 653 | 10/2002 |
| EP | 1291006 | 12/2003 |
| EP | 1470812 | 10/2004 |
| GB | 1125528 | 8/1968 |
| GB | 2 254 341 | 10/1992 |
| GB | 2 293 157 | 3/1996 |
| JP | 48-68750 | 9/1973 |
| JP | S49-050144 | 5/1974 |
| JP | 55-49308 | 4/1980 |
| JP | 58-30282 | 6/1983 |
| JP | 59-108710 | 6/1984 |
| JP | 61-143412 | 7/1986 |
| JP | 62-242609 | 1/1987 |
| JP | 62-242609 | 10/1987 |
| JP | 63-246313 | 10/1988 |
| JP | 04-99711 | 3/1992 |
| JP | 04-282307 | 10/1992 |
| JP | 04-293568 | 10/1992 |
| JP | 06-107530 | 4/1994 |
| JP | 06-271435 | 9/1994 |
| JP | 6-271435 | 9/1994 |
| JP | 07-23293 | 3/1995 |
| JP | 07-267834 | 10/1995 |
| JP | 07-330559 | 12/1995 |
| JP | 07-330560 | 12/1995 |
| JP | 08-40837 | 2/1996 |
| JP | 08-119839 | 5/1996 |
| JP | 08-165235 | 6/1996 |
| JP | 08-199188 | 8/1996 |

(Continued)

OTHER PUBLICATIONS

U.S. Appl. No. 12/739,091, filed Apr. 21, 2010, Fujinuma, et al.
U.S. Appl. No. 12/739,835, filed Apr. 26, 2010, Fujinuma, et al.
U.S. Appl. No. 12/739,610, filed Apr. 23, 2010, Fujinuma, et al.
U.S. Appl. No. 12/739,631, filed Apr. 23, 2010, Miyabe.
U.S. Appl. No. 12/739,471, filed Apr. 23, 2010, Miyabe, et al.
Notice of Submission of Publications issued Oct. 16, 2009 in Japanese Patent Application No. 2006-121135 filed Sep. 14, 2009.
U.S. Appl. No. 12/995,378, filed Nov. 30, 2010, Ogawa, et al.
Submission of Publications filed Oct. 18, 2010 in Japanese application No. 2004-130373 (w/English Translation).
Submission of Publications filed Oct. 25, 2010 in Japanese application No. 2008-270377 (w/English Translation).

(Continued)

*Primary Examiner* — Eisa B Elhilo
(74) *Attorney, Agent, or Firm* — Oblon, Spivak, McClelland, Maier & Neustadt, L.L.P.

(57) ABSTRACT

There is provided a head hair dyeing method using a two-part hair dye composition which contains: a first part containing a first part stock solution and a propellant, the first part stock solution containing an alkali agent and a surfactant; a second part containing a second part stock solution and a propellant, the second part stock solution containing hydrogen peroxide and a surfactant; and two aerosol containers for respectively discharging the first part and the second part as foam, the method including respectively discharging the first part and the second part as foam from the containers, applying the foam mixture to the head hair, and then re-foaming the mixture on the head hair.

4 Claims, No Drawings

FOREIGN PATENT DOCUMENTS

| | | |
|---|---|---|
| JP | 8-199188 | 8/1996 |
| JP | 08-230959 | 9/1996 |
| JP | 08-231345 | 9/1996 |
| JP | 8-231346 | 9/1996 |
| JP | 04-282307 | 10/1996 |
| JP | 08-259426 | 10/1996 |
| JP | 8-259426 | 10/1996 |
| JP | 08-268848 | 10/1996 |
| JP | 08-282308 | 10/1996 |
| JP | 8-283695 | 10/1996 |
| JP | 09-2923 | 1/1997 |
| JP | 09-2925 | 1/1997 |
| JP | 9-25223 | 1/1997 |
| JP | 09-40534 | 2/1997 |
| JP | 2579516 | 2/1997 |
| JP | 09-136818 | 5/1997 |
| JP | 09-136818 A | 5/1997 |
| JP | 09-143040 | 6/1997 |
| JP | 09-506130 | 6/1997 |
| JP | 09-227347 | 9/1997 |
| JP | 9-227347 | 9/1997 |
| JP | 09-234112 | 9/1997 |
| JP | 09 234112 | 9/1997 |
| JP | 09-255541 | 9/1997 |
| JP | 9-255541 | 9/1997 |
| JP | 9-301835 | 11/1997 |
| JP | 09-301835 | 11/1997 |
| JP | 10-25230 | 1/1998 |
| JP | 10-167938 | 6/1998 |
| JP | 10-287534 | 10/1998 |
| JP | 11-18836 | 1/1999 |
| JP | 11-18837 | 1/1999 |
| JP | 11-50089 | 2/1999 |
| JP | 11-124321 | 5/1999 |
| JP | 11-139945 | 5/1999 |
| JP | 11-199454 | 7/1999 |
| JP | 11-206454 | 8/1999 |
| JP | 11-286421 | 10/1999 |
| JP | 2000-191471 | 7/2000 |
| JP | 2000-297018 | 10/2000 |
| JP | 2000-297019 | 10/2000 |
| JP | 2001-10930 | 1/2001 |
| JP | 2001-19626 | 1/2001 |
| JP | 2001-97834 | 4/2001 |
| JP | 2001-172166 | 6/2001 |
| JP | 2001-278742 | 10/2001 |
| JP | 2001-288054 | 10/2001 |
| JP | 2001-327321 | 11/2001 |
| JP | 2002-20247 | 1/2002 |
| JP | 2002-97121 | 4/2002 |
| JP | 2002-154938 | 5/2002 |
| JP | 2002-193771 | 7/2002 |
| JP | 2002-220329 | 8/2002 |
| JP | 2002-226340 | 8/2002 |
| JP | 2002-226344 A | 8/2002 |
| JP | 2002-284655 | 10/2002 |
| JP | 03-12479 | 1/2003 |
| JP | 2003-26554 | 1/2003 |
| JP | 2003-40747 | 2/2003 |
| JP | 2003-63936 | 3/2003 |
| JP | 2003-73240 | 3/2003 |
| JP | 2003-73240 A | 3/2003 |
| JP | 2003-73241 | 3/2003 |
| JP | 2003-081791 A | 3/2003 |
| JP | 2003-95900 | 4/2003 |
| JP | 2004-339216 A | 12/2004 |
| JP | 2006-124279 A | 5/2006 |
| JP | 2007-119480 | 5/2007 |
| JP | 2007-291015 A1 | 11/2007 |
| JP | A1-2007-291015 | 11/2007 |
| JP | 2007-312523 A | 12/2007 |
| JP | 2007-314523 A1 | 12/2007 |
| JP | 2007-314524 | 12/2007 |
| JP | A1-2007-314523 | 12/2007 |
| JP | 2010-6803 | 1/2010 |
| JP | 2010-6805 | 1/2010 |
| WO | WO 91/14759 | 10/1991 |
| WO | WO 95/016023 | 6/1995 |
| WO | WO 01/85105 | 11/2001 |
| WO | WO 01/85113 | 11/2001 |
| WO | WO 2010/103795 | 9/2010 |
| WO | WO 2010103796 | 9/2010 |
| WO | WO 2011/065550 | 6/2011 |
| WO | WO 2011/066560 | 6/2011 |

OTHER PUBLICATIONS

Decision of Refusal issued Jun. 16, 2010 in Japanese application No. 2004-130373 (w/English Translation).
Written Demand for Appeal filed Sep. 10, 2010 in Japanese application No. 2004-130373 (w/English Translation).
Amendment filed Sep. 10, 2010 in Japanese application No. 2004-130373 (w/English Translation).
Submission of Publications filed Apr. 8, 2009 in Japanese application No. 2004-130373 (w/English Translation).
English Translation of Decision to Grant a Patent issued Jan. 4, 2011 in Japanese Patent application No. 2004-130373 w/Copy of Allowed Claims.
English Translation of Decision to Grant a Patent issued Jan. 4, 2011 in Japanese Patent application No. 2008-270377 w/Copy of Allowed Claims.
English translation of Submission of Publications filed Sep. 7, 2009 in Japanese application No. 2004-130373.
English translation of Submission of Publications filed Mar. 24, 2009 in Japanese application No. 2004-130373.
English translation of Notification of Reasons for Refusal issued Jul. 22, 2008 in Japanese application No. 2004-130373.
Remarks filed Feb. 25, 2011 in European Patent application No. 0 400 9836.0.
JP 10-287534 (Oct. 27, 1998) Abstract.
JP 9-227347 (Sep. 2, 2007) Abstract.
"Food and Packaging", Can Technology Study Group, vol. 34, No. 8, Aug. 1, 1993, 6 pages.
JP 2002-284655 (Oct. 3, 2002) Abstract.
JP 8-283695 (Oct. 29, 1996) Abstract.
Third-Party Observation filed on Apr. 27, 2011 in European Patent application No. 0 400 9836.0 (including translation of submission).
Office Action issued Jun. 15, 2011 in Chinese Patent Application No. 200780100733.0.
U.S. Appl. No. 13/107,183, filed May 13, 2011, Fujinuma, et al.
U.S. Appl. No. 13/146,157, filed Jul. 25, 2011, Iijima, et al.
Office Action issued Jun. 15, 2011 in corresponding Chinese Application No. 200780100733.0 (English translation).
Submission of Publications and the like, dated Nov. 10, 2008, in Japanese Patent Application No. 2004-130373.
Corresponding application filed in Japanese Application No. 2004-130373, filed on Nov. 10, 2008.
Japanese Patent Office Communication. Apr. 21, 2009, 3 pp. (includes statement submitted by third party).
Submission of Publications and the like, dated Mar. 24, 2009, in Japanese Patent Application No. 2004-130373. (with English translation).
Submission of Publication and the like, dated Sep. 7, 2009, in Japanese Patent Application No. 2004-130373.
Shinbiyo Marcel. Oct. 1996. No. 31, pp. 73 and 83. "Vivid Highlight" advertisement page (with partial English translation).
Vivid Highlight. Inya Cosmetics. Packaging and Instructions Insert. Sep. 6, 1996 (with English translation).
Hair Mode. Aug. 1996. No. 437. p. 108. (with partial English translation.
Decision to Refuse a European Patent Application issued Apr. 19, 2011, in regard to European Patent Application No. 08752171.2, filed Apr. 25, 2008.
Third-Party Observation submitted Jun. 3, 2011, in European Patent Application No. 10172766.7, filed Apr. 26, 2004.
Rompps Chemie Lexikon, vol. 6, 8th Ed. 1998. p. 4531.
Third-Party Observation submitted May 3, 2011, in European Patent Application No. 0 400 9836.0.
Extended European Search Report issued Apr. 7, 2011, in European Application No. 10183376.2.

European Patent Office Communication pursuant to Rule 114(2) EPC issued May 3, 2011, in European Application No. 04009836.0 filed Apr. 26, 2004.
Third-Party Observation filed on Apr. 27, 2011, in European Patent Application No. 0 400 9836.0 (including translation of submission).
"Food and Packaging," Can Technology Study Group. vol. 34, No. 8. Aug. 1, 1993. 6 pages.
Notification of Reason for Refusal, dated Jul. 22, 2008, in Japanese Patent Application No. 2004-130373.
English translation of Submission of Publication and the like, dated Dec. 25, 2007, in Japanese Patent Application No. 2004-130373.
English translation of Submission of Publication and the like, dated Feb. 29, 2008, in Japanese Patent Application No. 2004-130373.
Extended European Search Report issued in Nov. 4, 2010 in European Patent Application No. 10172766.7.
Taya-A.T. HM Education Mook., Series 3. "Knowing Mechanisms of Hair Coloring Agents." Apr. 10, 1998. pp. 8-9. (with English translation).
Nakanishi, Fumio. Fragrance Journal. "Future View of Hair Care Products." Jan. 15, 1997. pp. 49-56. (with English translation).
Sato, Takatoshi, et al. Fragrance and Cosmetics Science. "Permanent Hair Colorant." Sep. 20, 2001. pp. 138-140. (with English translation).
Watanabe, Yasushi, et al. Hair Science. "Hair Colorant." Feb. 1, 1986. pp. 144-150. (with English translation).
Submission of Publications and the like, filed Oct. 18, 2010 in Japanese application No. 2004-130373 (w/ English Translation).
Communication Pursuant to Article 94(3) EPC issued Nov. 5, 2010 in European Patent application No. 0 400 9836.0.
Submission of Publications and the like, filed Oct. 25, 2010 in Japanese application No. 2008-270377 (w/ English Translation).
Decision of Refusal issued Jun. 16, 2010 in Japanese application No. 2004-130373 (w/ English Translation).
Written Demand for Appeal filed Sep. 10, 2010 in Japanese application No. 2004-130373 (w/ English Translation).
Amendment filed Sep. 10, 2010 in Japanese application No. 2004-130373 (w/ English Translation).
Submission of Publications and the like, filed Apr. 8, 2009 in Japanese application No. 2004-130373 (w/ English Translation).
English Translation of Decision to Grant a Patent issued Jan. 4, 2011 in Japanese Patent application No. 2004-130373 w/ Copy of Allowed Claims.
English Translation of Decision to Grant a Patent issued Jan. 4, 2011 in Japanese Patent application No. 2008-270377 w/ Copy of Allowed Claims.
English translation of Remarks filed Oct. 20, 2008 in Japanese application No. 2004-130373.
English translation of Remarks filed Mar. 9, 2009 in Japanese application No. 2004-130373.
English translation of Amendment filed Mar. 9, 2009 in Japanese application No. 2004-130373.
European Search Report submitted Aug. 23, 2004, in European Patent Application No. 04009836.0.
English translation of Submission of Publications filed Nov. 10, 2008 in Japanese application No. 2004-130373.
English translation of Notification of Reasons for Refusal issued Jan. 6, 2009 in Japanese application No. 2004-130373.
English translation of Submission of Publications filed Dec. 25, 2007 in Japanese application No. 2004-130373.
English translation of Submission of Publications filed Feb. 29, 2008 in Japanese application No. 2004-130373.
Response to Communication Pursuant to Article 96(2) EPC filed Apr. 25, 2007 in European Patent application No. 0 400 9836.0.
Communication Pursuant to Article 94(3) EPC issued Dec. 29, 2008 in European Patent application No. 0 400 9836.0.
Response to Communication filed Jul. 8, 2009 in European Patent application No. 0 400 9836.0.
Third-Party Observation filed on Dec. 19, 2009 in European Patent application No. 0 400 9836.0.
Observations under Rule 114(2) EPC filed Apr. 9, 2010 in European Patent application No. 0 400 9836.0.
Third-Party Observation filed on May 10, 2010 in European Patent application No. 0 400 9836.0.

Communication Pursuant to Article 94(3) EPC issued Jun. 28, 2010 in European Patent application No. 0 400 9836.0.
Response to Communication filed Aug. 10, 2010 in European Patent application No. 0 400 9836.0.
Amendment filed Dec. 5, 2008 in European Patent application No. 0 400 9836.0.
Response to Communication filed Feb. 18, 2011 in European Patent application No. 0 400 9836.0.
Remarks filed Feb. 25, 2011 in European Patent application No. 08 752 171.2.
Experimental Report 1 (with English translation), served on May 24, 2011, in regard to Heisei 23 year (Yo) No22009.
Nakanishi, Fumio. Fragrance Journal. "Function of Recent Hair Coloring Agent and Developmental Trend Thereof." Aug. 15, 2001. pp. 39-45. (with English translation).
Yamagata, Yoshifumi, et al. Fragrance Journal. "Science of Foam: Function and Physical Properties of Foam." Dec. 15, 1992. pp. 37-47. (with English translation).
Yamakawa, Arata, et al. Fragrance Journal. "Development and Objective of Mousse Hair Cosmetic Products." Dec. 15, 1992. pp. 48-54. (with English translation).
Tashima, Masaru, et al. Fragrance Journal. "Research and Development of Mist Foam Type Hair Styling Product" Dec. 15, 1992. pp. 61-69. (with English translation).
Omura, Takayuki, et al. Fragrance Journal. "Development Trend and Problems of Recent Hair Foam." Mar. 15, 1994. pp. 29-35. (with English translation).
Miyagi, Takashi. Food and Packaging, vol. 34, No. 8. "Does Non-Gas Container Cause a Boom? (Part 2)" 1993. pp. 467-471. (with English translation).
Miyagi, Takashi. Food and Packaging, vol. 36, No. 3. Non-Gas Container Having Increased Level of Accomplishment (Part 3). 1995. pp. 154-158. (with English translation).
Prettia Product Information (with English Translation), Kao Corporation, published after Apr. 23, 2003. (served on May 25, 2011 in regard to Heisei 23 year (Yo) No. 22009).
Instructions for Feminine Treatment Hair Color (with English Translation), Feminine Co., Ltd., published before Apr. 23, 2003 (served on May 25, 2011 in regard to Heisei 23 year (Yo) No22009).
Feminine Treatment Hair Color 84, Certification for Approval for Manufacture of Quasi-Drug (with English Translation), Jan. 30, 1997.
Instructions for Feminine Retouch Color (with English Translation), Feminine Co., Ltd., published before Apr. 23, 2003. (served on May 25, 2011, in regard to Heisei 23 year (Yo) No. 22009).
Experimental Report 2 (with English translation), served on May 25, 2011, in regard to Heisei 23 year (Yo) No. 22009.
Experimental Report 3 (with English translation), served on May 25, 2011, in regard to Heisei 23 year (Yo) No. 22009.
Test Report 4 (with English translation), served on Jul. 10, 2011, in regard to Heisei 23 year (Yo) No. 22009.
Mottram, F.J., et al. Poucher's Perfumes, Cosmetics and Soaps, $10^{th}$ ed. © 2000. "Hair Shampoos." pp. 295-301.
Handbook "Poly Haarberater Coloration," original edition, 1992. pp. 76-77.
Third-Party Observation submitted May 12, 2011, in European Patent Application No. 04009836.0.
371-EPO Response in European Patent Application No. 04009836.0, Jul. 15, 2011.
Reply to EESR in European Patent Application No. 10172766.7, Apr. 29, 2011.
Third-Party Observation submitted Jun. 24, 2011, in European Patent Application No. 10172766.7.
Third-Party Observation submitted Jun. 24, 2011, in European Patent Application No. 10183376.2.
Photocopy of a folding, collapsible box for "Poly Brillance Intensiv-Color-Creme", dated as Aug. 25, 1997.
Instructions for use contained in the folding, collapsible box for "Poly Brillance Intensiv-Color-Creme" Aug. 25, 1997.
Entire contents of the folding, collapsible box for "Poly Brillance Intensiv-Color-Creme" Aug. 25, 1997.
Close-up photocopy of the folding, collapsible box for "Poly Brillance Intensiv-Color-Creme" Aug. 25, 1997.

Miyagi, Takashi. Foods and Containers, vol. 42, No. 10. "Growing Pump Foamer Spreading into Western Markets, Part One: Mini-Foamer." Oct. 1, 2001. pp. 609-613. (with English translation).
Kishi, Haruo. Modern Fragrance and Cosmetics Science, 1st Edition. Mar. 20, 1979. pp. 42-47. (with English translation).
Cosmetics Handbook. Nov. 1, 1996. pp. 220-221, 441-444. (with English translation).
Handbook—Raw Materials of Cosmetics and Drugs—revised edition. Feb. 1, 1977. pp. 358-361. (with English translation).
Yasuda, Kosaku, et al. Knowledge of Fat and Oil Products. Aug. 25, 1977. pp. 240-244. (with English translation).
Mitsui, Takeo. New Cosmetic Science. Jan. 12, 1993. pp. 137-142. (with English translation).
The Handbook of Oil Chemistry, 4th ed. "Lipids and Surfactants." Nov. 20, 2001. p. 522. (with English translation).
Comprehensive Dictionary of Chemistry. Oct. 20, 1989. pp. 56, 60-61, 646-647, 1762-1763. (with English translation).
Sato, Takatoshi, et al. Fragrance and Cosmetics Science. Mar. 20, 1997. pp. 73-74. (with English translation).
Japanese Collection of General Raw Materials for Cosmetics, fourth edition. Oct. 31, 1997. p. 583. (with English translation).
Analytical Chemistry Handbook, revised second edition. Oct. 10, 1971. pp. 27-29. (with English translation).
Analysis Methods for Surfactants. Oct. 1, 1975. pp. 117-118. (with English translation).
Chemical Daily. "Surfactant—Penetrated to the various fields taking advantage of unique characteristics." Jan. 21, 1999. (with English translation).
The Nikkan Kogyo Shimbun, Ltd. "Nonylphenol Identified as Endocrine Disrupting Chemical." Aug. 6, 2001. (with English translation).
Chemical Daily. "Surfactant—Started growing responding to safety requirement." Jan. 19, 2000. (with English translation).
Chemical Daily. "Surfactant—Remarkable performance of nonionic surfactant (Market conditions in chemicals)." Jan. 25, 2002. (with English translation).
Nakanishi, Fumio, et al. Science History of Hair Dye. Jan. 8, 1991. pp. 45-47. (with English translation).
Experiment Result Report 1 (with English translation), prepared on Jul. 11, 2011, in regard to No. 22009, 2011 (yo).
Experimental Result Report 2 (with English translation), prepared on Jul. 22, 2011, in regard to No. 22009, 2011 (yo).
Declaration by Akiko Nagabuchi (with English translation), served on Sep. 21, 2011, in regard to No. 22009, 2011 (yo).
Experiment Result Report 5 (with English translation), served on Sep. 21, 2011, in regard to No. 22009, 2011 (yo).
Arai, Yasuhiro. "State-of-the-art: Hair Color Technology—Trends in development as seen in patents." Published by Fragrance Journal Ltd. Aug. 25, 2004. pp. 102-105, 212-213. (with English translation).
Experimental Result Report 6 (with English translation), served on Sep. 21, 2011, in regard to No. 22009, 2011 (yo).
Experimental Result Report 7 (with English translation), served on Sep. 21, 2011, in regard to No. 22009, 2011 (yo).
Hayakawa, Masakatsu. Fragrance Journal. "Trends in the R&D of Hair Dyes and Issues to Address." No. 38 (vol. 7, No. 5) Sep. 25, 1979. pp. 41-44. (with English translation).
Written Argument filed by the Debtor (1/2) in the Case of Request for Provisional Disposition of Patent Right: No. 22056, 2011 (yo), served on Sep. 6, 2011. pp. 1-5, 29-34. (with partial English translation).
Amendments to the Claims in Japanese Patent Application No. 2010-268209, filed on Apr. 8, 2011. (with English translation).
Publication of Unexamined Patent Application JP 2003-81369, Mar. 19, 2003.
English translation of Submission of Publications and the like, filed Mar. 24, 2009, in Japanese Application No. 2004-130373.
English translation of Submission of Publications and the like, filed Nov. 10, 2008, in Japanese Application No. 2004- 130373.
English translation of Notification of Reasons for Refusal issued Jul. 22, 2008, in Japanese Application No. 2004-130373.
English translation of Submission of Publications and the like, filed Sep. 7, 2009, in Japanese Application No. 2004-130373.
English translation of Submission of Publications and the like, filed Feb. 29, 2008, in Japanese Application No. 2004-130373.
English translation of Submission of Publications and the like, filed Dec. 25, 2007, in Japanese Application No. 2004130373.
Extended Search Report issued Nov. 4, 2010, in European Application No. 10172766.7.
Submission of Publication issued Oct. 18, 2010, in JP Application No. 2004-130373 (with English translation).
Office Action issued Nov. 5, 2010, in EP Application No. 04 009 836.0.
Third Party Observation issued on May 3, 2011, in corresponding European Application No. 04 009 836.
Experimental Result Report 8 (with English translation), served on Nov. 29, 2011, in regard to No. 22009, 2011 (yo).
Fragrance Journal. vol. 19, No. 6. "Recent Progress of Hair Dyes and Problems in Research and Development." Jun. 15, 1991. pp. 26-27. (with English translation).
Miyagi, Takashi. Food and Packaging, vol. 34, No. 9. "Will Non-Gas Containers Create a Boom? (No. 3)" 1993. pp. 531-535. (with English translation).
Robbins, Clarence R. "Chemical and Physical Behavior of Human Hair, fourth edition." Jul. 10, 2006. pp. 221-231. (with English translation).
Iwakura, Ryouhei. "Present State and Problems of Hair Dyes." Fragrance Journal, Special Issue. No. 11, pp. 87-93. Dec. 25, 1990 (with English translation).
Ishikawa, Ryoji. Experimental Report, in regard to No. 22056, 2011 (yo). Dec. 28, 2011 (with English translation).
Declaration by Hattori, Nobuhito, in regard to No. 22056, 2011 (yo), served on Dec. 28, 2011 (with English translation).
Unichemy Corp. Experimental Report, in regard to No. 22056, 2011 (yo). Issued on Jun. 24, 2011 (with English translation).
Pharmaceutical Additive Dictionary, 2nd Edition. pp. 153-154, 203-205. Mar. 25, 2002. (with English translation).
Murata, Seishiro. Cosmetic Dictionary, 1st Edition. pp. 182-183, 666-667. Dec. 15, 2003. (with English translation).
Miyagi, Takashi. Food and Container, vol. 35, No. 10. pp. 588-593. 1994. (with English translation).
Miyagi, Takashi. Food and Container, vol. 35, No. 11. pp. 624-627. 1994. (with English translation).
Comprehensible Surfactant, first edition. Sep. 1, 2003. pp. 32-49. (with English translation).
Quasi Drugs Manufacturing Material Specification 2006, first edition. p. 527-528. Jun. 16, 2006 (with English translation).
Nakanishi, Fumio. Fragrance Journal. "Recent Progress and Prospective Problems in Hair Colorants and Hair Lighteners" vol. 25, No. 1. Jan. 15, 1997. pp. 49-56. (with English translation).
Sato, Takatoshi. Science of Cosmetics. Mar. 20, 1997. pp. 138-140. (with English translation).
Denavarre, Maison G. The Chemistry and Manufacture of Cosmetics, second edition, vol. 4. 1975. pp. 841-863.
Cosmetics Dictionary, first edition. Oct. 1, 1992. p. 373. (with English translation).
New Cosmetic Science, second edition. Jan. 18, 2001. pp. 152-153. (with English translation).
"Make Your Hair Beautiful by Correct Usage—Hair Coloring Abc, revised edition." Feb. 1, 2000. pp. 18-19. (with English translation).

* cited by examiner

HEAD HAIR DYEING METHOD

This application is a CIP of a U.S. application Ser. No. 12/739,835 (ABN), filed on Apr. 26, 2010, which is a 371 of PCT/JP07/01160 filed on Oct. 24, 2007.

FIELD OF THE INVENTION

The present invention relates to a head hair dyeing method using a two-part hair dye composition.

BACKGROUND OF THE INVENTION

While liquid or creamy hair dye compositions have been widely used so far, it is difficult to apply these compositions to the head hair evenly. In particular, in the case of consumers themselves applying a hair dye composition to their own head hair at the roots or on the back of the head, they need to acquire skills of, such as, "blocking" or using two mirrors facing each other ("two-mirror technique"), and a careful operation is required to apply the composition evenly.

Accordingly, discharging a composition as foam in order to simplify the hair dyeing operation has been proposed, and hair dyes of a two-part aerosol type and those of a one-part non-aerosol type are known, for example. However, those of a two-part aerosol type have such problems that uneven bleaching or uneven dyeing is likely to occur due to an inconsistent mixing ratio of a first part and a second part, a pressure-proof metal container or the like is oxidized and corroded by hydrogen peroxide, and the internal pressure of the pressure-tight container is excessively increased by degradation of hydrogen peroxide. Furthermore, since such a one-part non-aerosol type has no or weak bleaching ability, it is difficult to achieve a great change in the color tone by one procedure. Therefore, a problem arises, i.e., a hair dyeing operation tends to be cumbersome since a hair dye is required to be left to develop for a long time and the procedure is required to be repeated after application.

On the other hand, discharging a two-part hair dye composition as foam from a non-aerosol foamer container (e.g., Patent Documents 1 and 2) has been proposed. By discharging a mixture solution of a first part and a second part from a foamer container as foam, variation in the mixing ratio hardly occurs compared to conventional two-part aerosol hair dyes and a sufficient bleaching or hair dyeing ability may be obtained compared to conventional one-part non-aerosol hair dyes.

Meanwhile, all of these two-part aerosol hair dyes, one-part non-aerosol hair dyes and two-part non-aerosol hair dyes, by which the hair dyes are discharged as foam from foamer containers, still suffer a common problem, i.e., it is difficult to adjust foam quality by which easiness of discharging from a container and operatability on the head hair are well-balanced. To solve this problem, for example, Patent Document 3 proposes a composition that maintains adequate foam quality and has an excellent foam breaking property at the time of application to the hair. However, a careful operation is still required for even application, and an alternative dyeing method has been needed.

PRIOR ART DOCUMENTS

Patent Documents

[Patent Document 1] JP-A-2004-339216
[Patent Document 2] JP-A-2006-124279
[Patent Document 3] JP-A-2001-019626

SUMMARY OF THE INVENTION

The present invention provides a head hair dyeing method using a two-part hair dye composition which contains: a first part containing a first part stock solution and a propellant, the first part stock solution containing an alkali agent and a surfactant; a second part containing a second part stock solution and a propellant, the second part stock solution containing hydrogen peroxide and a surfactant; and two aerosol containers for discharging the first part and the second part as foam respectively, the method including discharging the first part and the second part as foam from the respective containers, applying the foam mixture to the head hair, and then re-foaming the mixture on the head hair.

DETAILED DESCRIPTION OF THE INVENTION

Depending on the property of foam formed with an aerosol foamer container, foam may disappear during application or exposure, and the mixture solution applied to the head hair easily drips down.

Furthermore, while it is so convenient that any skills such as blocking and two-mirror technique are not required, however, a high defoaming rate inhibits visualization of incomplete or uneven application to the hair in back of the head. Therefore, uneven hair dyeing may occur, the reason of which is different from those in the use of liquid or creamy hair dyes.

The present invention relates to a head hair dyeing method, by which a two-part hair dye composition, foamed by using an aerosol foamer container, does not drip down between the applying to the head hair and the rinsing off, and incomplete or uneven application is avoided.

The inventors of the present invention found a head hair dyeing method that satisfy the above-described requirements, the method including applying a two-part hair dye composition discharged as foam on the head hair by using an aerosol container and the two-part hair dye composition and re-foaming the applied foam on the head hair thereafter.

According to the present invention, since the applied foam is re-foamed on the head hair, foam of a two-part hair dye composition can be rapidly and reliably spread over to the roots of the head hair without blocking, even the hair in back of the head, a part which is difficult to check, while avoiding incomplete or uneven application without using mirrors. In addition, dripping can be prevented irrespective of the foam property that may be varied depending on the structure of an aerosol container or the composition of a two-part hair dye composition.

DEFINITION

In the present invention, the head hair refers to the hair grown on the head, and the concept thereof does not include the hair separate from the head such as a wig and a tress. Furthermore, the head hair may be the hair of a doll or any animal, but human head hair is preferred.

In the present invention, a two-part hair dye composition is a concept including both a hair dye composition that contains a dye and a bleach composition that does not contain a dye. Furthermore, the head hair dyeing method is a concept including a head hair bleaching method.

In the present specification, the "stock solution" refers to the whole ingredients other than a propellant in an aerosol container.

Since a two-part aerosol foamy hair dye is required to mix a first part and a second part immediately before use, the first part and the second part are each required to be contained in separate aerosol containers together with a propellant. Accordingly, when the first part and the second part are discharged by the pressure of the propellant from the separate aerosol containers, the foams of the first part and the second part are separately formed by vaporization of the propellant. The separately formed foams are mixed before application to the head hair or on the head hair after application. During this mixing, the vaporized propellant dissipates, whereas the remaining stock solutions of the first part and the second part are mixed after temporarily getting back to a stock solution state or in this foam state. In consideration of such an actual status of use, the "mixture solution" simply described only in the present specification refers to a solution containing a mixture of stock solutions of the first part and the second part, for the sake of convenience (although there is no instance herein where the stock solutions of the first part and the second part present in the separate aerosol containers are mixed in a container). Likewise, foam formed by mixing foams of the first part and the second part are also simply referred to as "foam of a mixture solution" only in the present specification, for the sake of convenience.

[Aerosol Containers]

A first aerosol container containing a first part stock solution and a propellant and a second aerosol container containing a second part stock solution and a propellant may be made of any material so long as they include a mechanism that discharges the stock solution as foam, resist the pressure of the propellant, and are suitable for storage. Examples thereof include glass bottles and metal cans. For the metal cans, it is preferable to use double containers having an inner pouch attached to the inner surface of the can to prevent the can from corroding due to the contents.

The aerosol containers preferably have an internal pressure (20° C.) of 0.01 to 2 MPa, more preferably 0.02 to 1.5 MPa, even more preferably 0.05 to 1 MPa. Both the first part and the second part preferably have a stock solution:propellant mass ratio of 99:1 to 80:20, more preferably 98:2 to 82:18, even more preferably 95:5 to 85:15 from viewpoints that foam easily applied to the head hair can be obtained, the foams of the first part and the second part are uniformly miscible with each other, and re-foam operation is easily performed.

[Head Hair Dyeing Procedures]

It is preferable to shake aerosol containers before respective discharge of a first part and a second part from the aerosol containers, from viewpoints that a stock solution and a propellant in each aerosol container are favorably mixed, and the first part and the second part discharged from the respective aerosol containers form foam easily applied to the head hair.

The extent to which the aerosol containers are shaken is reciprocal shaking preferably at a rate of 0.5 to 5 strokes, more preferably 1 to 4 strokes, even more preferably 2 to 3 strokes, per second. The shaking amplitude is preferably shaken 5 to 50 cm, more preferably 10 to 40 cm, even more preferably 20 to 30 cm. The number of times they are shaken reciprocally is preferably 2 to 20 strokes, more preferably 3 to 15 strokes, even more preferably 4 to 10 strokes. Then, it is preferable to discharge the hair dye without waiting a time interval (preferably within 10 minutes, more preferably within 5 minutes, even more preferably within 3 minutes).

A two-part aerosol foamy hair dye is used for hair dyeing treatment by mixing a first part and a second part immediately before use. The first part and the second part of the two-part aerosol foamy hair dye are each contained in separate aerosol containers. The first part and the second part separately form foam with volatilization of the propellant upon being discharged out of the aerosol containers. For these reasons, in the present invention, the first part and the second part may be mixed by any of the following procedures:

1) once foaming the first part and the second part separately and then mixing by joining the foams together within the product;

2) separately discharging the first part and the second part from the aerosol containers as foam and then mixing them before applying to the head hair;

3) separately discharging the first part and the second part from the aerosol containers as foam and then mixing them upon application to the head hair;

4) separately discharging the first part and the second part from the aerosol containers as foam and then mixing them on the head hair after applying to the head hair.

The first part and the second part are preferably mixed at a ratio of about 2:1 to 1:2, more preferably almost 1:1, in terms of the amounts of their stock solutions.

[Specific Procedures]

In the head hair dyeing method of the present invention, it is preferable to comb the head hair in advance of application of discharged foam. Consequently, the hair hardly gets tangled during the re-foaming treatment, so that the hair dye composition is not likely to splatter. Furthermore, after the head hair is combed, blocking, generally performed in application of a hair dye composition, is not required, and it is preferable not to perform blocking. Consequently, the hair dye composition is easily applied to the head hair or re-foamed as described later.

From viewpoints of even hair dyeing, prevention of dripping, and a sufficient hair dyeing effect, it is preferable that hair dressing is not applied to the head hair to which the hair dye composition is to be applied immediately before the hair dyeing. Furthermore, from viewpoints that the mixture solution is not diluted even hair dyeing can be provided, dripping may be prevented and a sufficient hair dyeing effect may be obtained, dry head hair is preferred. When the hair is washed immediately before the hair dyeing treatment, it is preferable to dry the head hair before hair dyeing treatment. Drying the head hair means that the liquid, mainly water, attached due to the hair wash is removed at least to the extent that it does not drip in a spontaneous state. Specifically, it is preferable to dry the hair with a towel or a dryer.

Foams of the first part and the second part discharged from the aerosol containers are applied to the head hair after placing it on the hands or a brush, or directly. Here, when hands are used, it is preferable to wear gloves. According to the dyeing method of the present invention, since blocking generally performed in the application of a hair dye composition is not required, the foam may be applied in a short time. Therefore, the application of foam may be started at any head hair site, and it is not necessary to apply it starting with the neckline unlike conventional liquid or creamy two-part hair dye compositions. It is sufficient to start the application at a concerned portion, and it is preferable to apply foam from the hairline of the head hair or a site where the hair is parted.

It is preferable that foams of the first part and the second part joined together have about the size of a lemon to that of a tennis ball because it is the proper size to place on one hand and to easily apply to the head hair using hands. In this case, foam is discharged with one hand and received with the other hand. Then, after foam received on the hand is once applied to the head hair, foam is discharged on the hand again to repeat the application to the head hair. This series of operations may be performed very conveniently in a short period.

Furthermore, foam may be applied to the whole head hair or only a specific portion.

Then, the applied foam is re-foamed on the head hair. The foam may be re-foamed by injecting a gas, using an instrument such as a vibrator or a brush, or with fingers. However, since the two-part hair dye composition may be thoroughly spread to the roots of the head hair, it is more preferable to use fingers. The rate of foaming using a vibrator or a brush or with fingers is preferably controlled so that the foam does not spatter.

Here, the timing of re-foaming may be after the foam has disappeared completely, during the process of disappearance, or before the applied foam changes. Alternatively, the timing may be after the foam has been completely applied to the area that needs applying the foam or during the process of application. Re-foaming may be performed continuously once or intermittently in several times. Here, when a vibrator, a brush, or fingers used for re-foaming remain in contact with a part of the head hair, or they are brought into contact within 1 second even if they are once separated, the re-foaming is assumed as continuous. In short, it is sufficient to observe the applied site and suitably foam at least before liquid drips from the applied foam. Irrespective of the property of the foam, dripping may be prevented by re-foaming the foam that almost disappears. Furthermore, by re-foaming, foam may be changed to the quality suitable for hair dyeing regardless of differences in the structure of the aerosol container or the property of the foam depending on the composition of the two-part hair dye composition. In some cases, dripping may be prevented, and the foam quality suitable for hair dyeing may be maintained as it is by using a specific structure of the aerosol container or a specific composition of the two-part hair dye composition. Even in such cases, however, it is preferable to perform re-foaming at least once as early as possible after the completion of the foam application. By performing re-foaming at an early stage, uneven coloring in an area that needs applying may be prevented. This timing is preferably within 5 minutes after the completion of application of the discharged foam to the head hair, more preferably within 3 minutes, even more preferably within 1 minute.

Hereafter, specific examples of preferred procedures in the processes from discharge of foam to application to the head hair and re-foaming will be shown according to partial hair dyeing and whole head hair dyeing.

[Partial Hair Dyeing]

1) Discharge a suitable amount of foam on one hand, apply the foam to a part of the head hair, and perform one operation of re-foaming over 1 second to 10 minutes, preferably 3 seconds to 3 minutes.

2) Discharge a suitable amount of foam on one hand, apply the foam to a part of the head hair, perform one operation of re-foaming over 1 second to 10 minutes, preferably 3 seconds to 3 minutes, and repeat the operation 2 to 30 times. Re-foaming is performed over a total of 2 seconds to 20 minutes, preferably 5 seconds to 5 minutes.

[Whole Head Hair Dyeing]

3) Discharge a suitable amount of foam on one hand, apply the foam to a part of the head hair, and perform one operation of re-foaming over 3 seconds to 10 minutes, preferably 5 seconds to 3 minutes. Repeat this operation to apply the foam over the whole head.

4) Discharge a suitable amount of foam on one hand, apply the foam to a part of the head hair, and perform one operation of re-foaming over 3 seconds to 10 minutes, preferably 5 seconds to 3 minutes. Repeat this operation to apply the foam over the whole head, and then perform one operation of re-foaming over 3 seconds to 10 minutes, preferably 5 seconds to 3 minutes. Further, discharge a suitable amount of foam on one hand, additionally apply the foam to a part of the head hair, and perform one operation of re-foaming over the whole head over 3 seconds to 10 minutes, preferably 5 seconds to 3 minutes.

5) Discharge a suitable amount of foam on one hand, apply the foam to a part of the head hair, and perform one operation of re-foaming over 3 seconds to 10 minutes, preferably 5 seconds to 3 minutes. Repeat this operation to apply the foam over the whole head. After completion of the application to the whole head, perform one operation of re-foaming over 3 seconds to 10 minutes, preferably 5 seconds to 5 minutes.

6) Discharge a suitable amount of foam on one hand, apply the foam to a part of the head hair, and perform one operation of re-foaming over 3 seconds to 10 minutes, preferably 5 seconds to 3 minutes. Repeat this operation to apply the foam over the whole head. After completion of the application to the whole head, perform one operation of re-foaming over the whole head over 3 seconds to 10 minutes, preferably 5 seconds to 3 minutes, and repeat the operation 2 to 30 times. Re-foaming is performed over a total of 6 seconds to 20 minutes, preferably 10 seconds to 5 minutes.

7) Discharge a suitable amount of foam on a brush, and apply the foam to a part of the head hair. Repeat this operation to apply the foam over the whole head, and perform one operation of re-foaming over the whole head using the same brush over 3 seconds to 10 minutes, preferably 5 seconds to 5 minutes.

8) Discharge a suitable amount of foam on a brush, apply the foam to a part of the head hair, and perform one operation of re-foaming using the same brush or hands over 3 seconds to 10 minutes, preferably 5 seconds to 3 minutes. Repeat this operation to apply the foam over the whole head. After completion of application to the whole head, perform one operation of re-foaming using the same brush or hands over 3 seconds to 10 minutes, preferably 5 seconds to 5 minutes.

The area for re-foaming may be the whole head hair or only a specific portion. Since foam may be thoroughly spread by performing re-foaming over the whole head hair, incomplete dyeing may be prevented even if application of foam is missed at a site that may be hardly checked, such as the hair in back of the head. In partial dyeing, when re-foaming is performed on only a specific portion, the border of a dyed portion may be made unclear, and natural finishing is provided. Furthermore, when re-foaming is performed, it is very easy to visually check portions where foam has spread. Therefore, incomplete dyeing of a portion that needs dyeing may be avoided.

After completion of the foam application, the hair is washed after the foam is left for about 3 to 60 minutes, preferably about 5 to 45 minutes. In the present invention, the above-mentioned time after completion of the foam application means all the required time from completion of application of all the foam to the whole head or a desired portion to rinsing off, and is a concept including time required for re-foaming in addition to the time for simply leaving the hair. Then, the hair is suitably washed with a shampoo or treated with a conditioner, then rinsed with water, and dried.

[Two-Part Hair Dye Composition]

The two-part hair dye composition used in the present invention contains an alkali agent in a first part and hydrogen peroxide in a second part, and a surfactant and a propellant in both the first part and the second part. Further, a higher alcohol or a nonvolatile hydrophilic solvent is preferably contained in at least either of the first part or the second part, preferably in both parts.

[Alkali Agent]

Examples of the alkali agent contained in the first part include ammonia, alkanolamine such as ethanolamine, sodium hydroxide, and potassium hydroxide. Furthermore, ammonium salt such as ammonium hydrogen carbonate and ammonium chloride, carbonate such as potassium carbonate and sodium hydrogencarbonate, and the like may be suitably added as buffer.

pH of the mixture solution of the first part stock solution and the second part stock solution in the two-part hair dye composition used in the present invention is preferably 8 to 11, more preferably 9 to 11, and the amount of the alkali agent used is suitably adjusted so that the mixture solution has the above-mentioned pH.

[Hydrogen Peroxide]

The content of hydrogen peroxide in the second part stock solution is preferably 1 to 9% by mass, more preferably 3 to 6% by mass. The content of hydrogen peroxide in the mixture solution of the first part stock solution and the second part stock solution is preferably 1 to 6% by mass, more preferably 2 to 5% by mass. Further, the pH of the second part stock solution is preferably 2 to 6, more preferably pH 2.5 to 4, to prevent degradation of hydrogen peroxide.

[Surfactant]

A surfactant is added to both the first part stock solution and the second part stock solution, so that foam is easily formed by a foam discharging means of an aerosol container, and that the foam is stable. An anionic surfactant and/or a nonionic surfactant is preferably used so that favorable foam that is readily applied to the head hair can be provided even when a solution temperature is low or close to ordinary temperature.

Examples of the anionic surfactant include, such as, a sulfuric acid ester type, sulfonic acid type, carboxylic acid type and phosphate ester type anionic surfactants. Preferred examples thereof include alkylsulfate and polyoxyalkylene alkylsulfate of the sulfuric acid ester type, with an alkyl group having 10 to 24 carbon atoms, more preferably 12 to 18 carbon atoms. Furthermore, this alkyl group is preferably linear. Furthermore, of the polyoxyalkylene alkylsulfate, polyoxyethylene alkylsulfate is more preferred. Of these, those with an oxyethylene group having an average number of additional moles of 1 to 10, more preferably 2 to 5 are preferred.

Examples of the nonionic surfactant include polyoxyalkylene alkyl ether, polyoxyalkylene alkenyl ether, polyoxyalkylene fatty acid ester, alkylglyceryl ether, polyglycerine fatty acid ester, fatty acid alkanol amide, sugar ether type, sugar ester type, and sugar amide type. Preferred examples thereof include alkyl polyglycoside, polyoxyalkylene alkyl ether and alkylglyceryl ethers. Alkyl polyglycoside preferably include an alkyl group having 8 to 18 carbon atoms, more preferably 8 to 14, even more preferably 9 to 11, and this alkyl group is preferably linear. The average degree of polymerization of a glucoside is preferably 1 to 5, more preferably 1 to 2. Polyoxyalkylene alkyl ether is preferably an ether having an alkyl group having 10 to 22 carbon atoms, more preferably 12 to 18, and this alkyl group is preferably linear. Furthermore, polyoxyethylene alkyl ethers are more preferred, and of these, the average added number of oxyethylene group is 1 to 40, more preferably 4 to 30. Alkylglyceryl ethers preferably include an alkyl group having 8 to 18 carbon atoms, more preferably 8 to 12, and this alkyl group is preferably branched.

Two or more types of surfactant may be used in combination, and the content thereof in the first part stock solution and the second part stock solution is preferably 1 to 15% by mass, more preferably 2 to 10% by mass, even more preferably 2.5 to 7% by mass, even more preferably 3 to 5% by mass.

Furthermore, to improve the discharged foam quality at a low solution temperature and prevent dripping, it is preferable to use an anionic surfactant and a nonionic surfactant in combination, and the mass ratio of the anionic surfactant to the nonionic surfactant in each stock solution (content of anionic surfactant/content of nonionic surfactant) is preferably 0.01 to 1, more preferably 0.1 to 0.5.

When the two-part hair dye composition used in the present invention is used for dyeing of the head hair, an oxidative dye or a direct dye is added to the first part. To solubilize these dyes, it is preferable to mainly use nonionic surfactant as surfactant added to the first part, taking into account the high ionic strength of ammonia and carbonates contained in the first part. On the other hand, anionic surfactants are preferably added to the second part due to the high ionic strength of the first part.

[Propellant]

The propellant is an agent for discharging the contained hair dye as foam from the aerosol containers, and any propellant generally used can be used. Examples thereof include liquefied petroleum gas (LPG), dimethyl ether (DME), carbon dioxide gas, nitrogen gas, and mixtures thereof. Moreover, chlorofluorocarbon substitutes such as HFC-152a may be used. Of them, liquefied petroleum gas (LPG), dimethyl ether (DME), or a mixture thereof is preferable from viewpoints that the viscosity of each hair dye stock solution is reduced, and the hair dye is easily re-foamed. The propellant more preferably contains dimethyl ether (DME). The content of dimethyl ether (DME) in the propellant is preferably 1 to 99% by mass, more preferably 2 to 97% by mass, even more preferably 5 to 95% by mass.

[Higher Alcohol]

It is preferable that the two-part hair dye composition used in the present invention contain a higher alcohol in at least either of the first part stock solution or the second part stock solution, preferably in both stock solutions to allow foam to be maintained longer and to improve the effect of preventing dripping during the foam being left to develop after application of a two-part hair dye composition to the head hair. Higher alcohols preferably include an alkyl or alkenyl group having 10 to 30 carbon atoms, more preferably 12 to 24 carbon atoms, even more preferably 14 to 22. Of these, those including an alkyl group, more preferably a linear alkyl group are preferred. Examples of the higher alcohol include myristyl alcohol, cetanol, stearyl alcohol, behenyl alcohol, isostearyl alcohol, and oleyl alcohol. Two or more thereof may be used in combination.

Two or more types of higher alcohols may be used in combination. The content of the higher alcohol in the first part stock solution or the second part stock solution is preferably 0.05 to 1% by mass, more preferably 0.1 to 0.8% by mass, even more preferably 0.2 to 0.6% by mass, even more preferably 0.3 to 0.4% by mass from viewpoints that foaming property is not deteriorated at a low solution temperature, and the effect of preventing dripping during the foam being left to develop is improved.

In the present invention, the mass ratio of the higher alcohol to the surfactant (content of higher alcohol/content of surfactant) in each stock solution is preferably 0.02 to 0.4, more preferably 0.03 to 0.3, even more preferably 0.05 to 0.2 to improve the foam quality at a low solution temperature and to prevent dripping.

[Nonvolatile Hydrophilic Solvent]

Furthermore, it is preferable that the two-part hair dye composition used in the present invention contain a nonvolatile hydrophilic solvent in at least either of the first part stock solution or the second part stock solution, preferably in both stock solutions. Consequently, irritation on the scalp may be reduced which occurs because water is evaporated from the two-part hair dye composition while leaving to develop after application of the two-part hair dye composition to the head hair, and therefore irritating components such as hydrogen peroxide are concentrated. Preferred examples of the nonvolatile hydrophilic solvent include substances without a defoaming action such as polyols and lower alkyl ethers (having 1 to 4 carbon atoms) derived therefrom. Polyols having 2 to 6 carbon atoms are preferred, and examples thereof include glycerin, diglycerin, propylene glycol, dipropylene glycol, 1,3-butane diol, ethylene glycol, diethylene glycol, isoprene glycol, and sorbitol. Examples of lower alkyl ether derived from polyol include mono-lower alkyl ethers and poly-lower alkyl ethers derived from the above-mentioned polyols (e.g., di-lower alkyl ether). Of these, mono-methyl ether and mono-ethyl ether derived from polyols are preferred, and specific examples thereof include ethylene glycol mono-methyl ether, ethylene glycol mono-ethyl ether, diethylene glycol mono-methyl ether, and diethylene glycol mono-ethyl ether. Two or more thereof may be used in combination.

The content of the nonvolatile hydrophilic solvent in the first part stock solution or the second part stock solution is preferably 0.1 to 4% by mass, more preferably 0.5 to 3% by mass, even more preferably 1 to 2% by mass, from viewpoints that irritation of the scalp is reduced, and that favorable foam quality is maintained even at a low solution temperature.

Not to cause irritation to the scalp even when the content of the nonvolatile hydrophilic solvent is reduced and to maintain a hair dyeing ability and a bleaching ability, the mass ratio of the surfactant to the nonvolatile hydrophilic solvent (content of surfactant/content of nonvolatile hydrophilic solvent) in each stock solution is preferably 1 to 20, more preferably 1 to 10, even more preferably 1.5 to 5, even more preferably 2 to 4.

[Polyquaternium-7]

Polyquaternium-7 may be further added to at least either of the first part stock solution or the second part stock solution, preferably both stock solutions of the two-part hair dye composition used in the present invention to improve the effect of preventing dripping. As Polyquaternium-7, commercially available products such as, for example, Merquat 550 (Nalco) may be used.

The content of Polyquaternium-7 in the first part or the second part is preferably 0.01 to 3% by mass, more preferably 0.1 to 1% by mass, even more preferably 0.2 to 0.5% by mass to realize favorable foam that is easily applied to the head hair even when the solution temperature is low or close to ordinary temperature, and to obtain an effect of preventing the mixture solution from dripping down between applying to the hair and rinsing off.

[Polyquaternium-22]

Polyquaternium-22 may be further added to at least either of the first part stock solution or the second part stock solution, preferably both stock solutions of the two-part hair dye composition used in the present invention to control the defoaming property after application to the hair, maintain adequate residual foam, and easily check applied sites. As Polyquaternium-22, commercially available products such as, for example, Merquat 280 and Merquat 295 (both produced by Nalco) may be used.

The content of Polyquaternium-22 in the first part stock solution or the second part stock solution is preferably 0.01 to 0.5% by mass, more preferably 0.1 to 0.2% by mass to obtain the above-described effects without deteriorating the foaming property at a low solution temperature.

[Dyes]

The two-part hair dye composition of the present invention may be used for bleaching of the head hair when a dye is not added, and also may be used for hair dyeing when an oxidative dye or a direct dye is added. When the composition is used for hair dyeing, the first part contains an oxidative dye and/or a direct dye. Examples of the oxidative dye include dye precursors such as p-phenylenediamine, toluene-2,5-diamine, o-chlor-p-phenylenediamine, N-phenyl-p-phenylenediamine, N,N-bis(hydroxyethyl)-p-phenylenediamine, 3-methyl-4-aminophenol, 2-hydroxyethyl-p-phenylenediamine, p-aminophenol, p-methylaminophenol, 4-amino-m-cresol, o-aminophenol, 1-hydroxyethyl-4,5-diaminopyrazole, and salts thereof; and couplers such as resorcin, 2-methylresorcin, 1-naphthol, 1,5-dihydroxynaphthalene, 5-amino-o-cresol, m-phenylenediamine, m-aminophenol, 2,4-diaminophenoxyethanol, 2,6-diaminopyridine, 2-methyl-5-hydroxyethylaminophenol, 2-amino-3-hydroxypyridine, and salts thereof.

Examples of the direct dye include basic dyes, nitro dyes, dispersive dyes, and cationic dyes. More specific examples thereof include 2-nitro-p-phenylenediamine, 2-amino-6-chloro-4-nitrophenol, 3-nitro-p-hydroxyethylaminophenol, 4-nitro-o-phenylenediamine, 4-amino-3-nitrophenol, 4-hydroxypropylamino-3-nitrophenol, HC Blue 2, HC Orange 1, HC Red 1, HC Yellow 2, HC Yellow 4, HC Yellow 5, HC Red 3, N,N-bis(2-hydroxyethyl)-2-nitro-p-phenylenediamine, Dispersive Purple 1, Dispersive Blue 1, Dispersive Black 9, Basic Blue 99, Basic Brown 16, Basic Brown 17, Basic Red 76, Basic Yellow 76, Basic Orange 31, Basic Red 51 etc.

[Silicones]

It is preferable that silicone be added to neither the first part stock solution nor the second part stock solution in the two-part hair dye composition used in the present invention from a viewpoint that discharged foam may be maintained for a long time. However, silicone may be contained to a certain extent in either the first part stock solution or the second part stock solution, preferably in both stock solutions to work the foam into the head hair smoothly and exert a high conditioning effect on the head hair. Examples of the silicones include dimethylpolysiloxane, methylphenylpolysiloxane, polyether-modified silicone, amino-modified silicone, and oxazoline-modified silicone elastomer, and emulsion obtained by dispersing these silicones in water using surfactants. Of these, polyether-modified silicone, amino-modified silicone, and emulsion thereof are preferred, from a viewpoint that a stable dispersion in water is enabled without using a thickening agent.

When silicones are used for the above-described purpose, the content of the silicones in the mixture solution of the first part stock solution and the second part stock solution is preferably 0.01 to 0.5% by mass, more preferably 0.02 to 0.4% by mass, even more preferably 0.05 to 0.3% by mass.

[Other Components]

In addition, depending on the purposes, fragrance, ultraviolet absorber, metal sequestering agent such as edetic acid, disinfectant, preservative such as methyl paraoxybenzoate, stabilizer such as fenasetin, etidronic acid, and oxyquinoline sulfate, organic solvent such as ethanol, benzyl alcohol, and benzyloxyethanol, water-soluble polymer such as Polyquaternium-6, Polyquaternium-39, and hydroxyethylcellulose, moisturizing agent and the like may be added to the first part stock solution and the second part stock solution. Furthermore, using water as the main medium in the mixture solution of the first part and second part is preferable.

[Viscosity]

The viscosities of the first part stock solution and the second part stock solution are each preferably 1 to 8000 mPa·s, more preferably 5 to 6000 mPa·s, even more preferably 10 to 4000 mPa·s from viewpoints that foam is well worked into the head hair after separate discharge of the first part and the second part from the aerosol containers and application to the head hair such that the hair dye sufficiently penetrates the head hair to secure favorable dyeability and to enhance ease of re-foaming, and foam formed by re-foam is easily spreadable.

The viscosity of a mixture solution of the first part stock solution and the second part stock solution mixed in the whole amounts is preferably 1 to 10000 mPa·s, more preferably 5 to 8000 mPa·s, even more preferably 10 to 5000 mPa·s from viewpoints that foam is well worked into the head hair after application to the head hair such that the hair dye sufficiently penetrates the head hair to secure favorable dyeability and to enhance ease of re-foaming, and foam formed by re-foam is easily spreadable.

It is noted that the viscosity refers to a value measured using a Brookfield viscometer (a rotational speed of 30 rpm, 60 sec., 30° C.). Measurement is performed from Rotor No. 1. When the measurement value exceeds the upper limit, Rotor No. 2 is used; however, when the measurement value still exceeds the upper limit, Rotor No. 3 is used; and however, when the measurement value still exceeds the upper limit, Rotor No. 4 is used. When measurement is achieved within the measuring range of each rotor, the obtained value is used as a measurement result without further using the subsequent rotor. Moreover, measurement is performed in a thermostat bath set to the measurement temperature. A container in which the object to be measured is injected in advance is left in the thermostat bath to adjust the temperature of the object to the measurement temperature. Measurement for the mixture solution is preformed after obtainment of a uniform mixture solution by mixing the first part and the second part immediately before measurement. The heat of reaction may be generated due to mixing to allow the temperature of the mixture solution to deviate from the measurement temperature. However, this change in temperature caused by the heat of reaction is ignored.

EXAMPLES

Examples 1 to 11

A first part stock solution and a second part stock solution of a two-part hair dyeing composition having the compositions shown in each of Tables 1 to 6 are prepared. The stock solution and a propellant are filled at a mass ratio of 90:10 in each aerosol container. The propellant used is LPG with a pressure of 0.20 MPa (20° C.). The amount of the stock solution is set to 50 g for both the first part and the second part (100 g in total).

TABLE 1

| First part | Content in first part (% by mass) |
| --- | --- |
| Para-aminophenol | 0.8 |
| Meta-aminophenol | 0.2 |
| Toluene-2,5-diamine | 0.5 |
| Resorcin | 0.6 |
| Aqueous ammonia (25% by mass) | 8.5 |
| Ammonium hydrogen carbonate | 8.0 |

TABLE 1-continued

| | |
| --- | --- |
| Decylglucoside | 3.2 |
| Laureth-23 | 2.0 |
| Propylene glycol | 4.0 |
| Polyquaternium-22 | 0.4 |
| Methylparaben | 0.1 |
| EDTA-4Na | 0.1 |
| Fragrance | 0.5 |
| Ascorbic acid | 0.3 |
| Anhydrous sodium sulfite | 0.4 |
| Water | Balance |

| Second part | Content in second part (% by mass) |
| --- | --- |
| Sodium laureth sulfate | 1.9 |
| Lauramide propyl betaine | 0.05 |
| Lauryl hydroxysultaine | 0.05 |
| Lauric acid | 0.04 |
| Cetanol | 1.5 |
| Etidronic acid | 0.04 |
| Phosphoric acid (75% by mass) | Amount required to adjust pH to 3.8 |
| Sodium hydroxide solution (48% by mass) | 0.01 |
| Oxyquinoline sulfate | 0.04 |
| Glycerine | 5.0 |
| Aqueous hydrogen peroxide (35% by mass) | 16.3 |
| Water | Balance |

TABLE 2

| First part | Content of first part (% by mass) |
| --- | --- |
| Toluene-2,5-diamine | 0.14 |
| Para-aminophenol | 0.1 |
| Meta-aminophenol | 0.05 |
| Para-amino-ortho-cresol | 0.1 |
| 2,4-Diaminophenoxyethanol hydrochloride | 0.15 |
| Aqueous ammonia (28% by mass) | 6.0 |
| Ammonium hydrogen carbonate | 10.5 |
| Decylglucoside | 6.5 |
| Trideceth-9 | 0.6 |
| Laureth-23 | 1.8 |
| Myristyl alcohol | 0.2 |
| Propylene glycol | 4.0 |
| Ethanol | 9.0 |
| Polyquaternium-7 | 0.6 |
| Polyquaternium-22 | 0.4 |
| EDTA-4Na | 0.1 |
| Ascorbic acid | 0.3 |
| Anhydrous sodium sulfite | 0.4 |
| Fragrance | 0.5 |
| Water | Balance |

| Second part | Content in second part (% by mass) |
| --- | --- |
| Sodium laureth sulfate | 1.9 |
| Lauramide propyl betaine | 0.05 |
| Lauryl hydroxysultaine | 0.05 |
| Lauric acid | 0.04 |
| Cetanol | 1.5 |
| Etidronic acid | 0.04 |
| Phosphoric acid (75% by mass) | Amount required to adjust pH to 3.8 |
| Sodium hydroxide solution (48% by mass) | 0.01 |
| Oxyquinoline sulfate | 0.04 |
| Glycerine | 5.0 |

TABLE 2-continued

| | |
|---|---|
| Aqueous hydrogen peroxide (35% by mass) | 16.3 |
| Water | Balance |

TABLE 3

| (% by mass) | Example | | | | |
|---|---|---|---|---|---|
| | 3 | 4 | 5 | 6 | 7 |
| First part | | | | | |
| Para-aminophenol | 0.15 | 0.15 | 0.15 | 0.15 | 0.15 |
| Para-amino-ortho-cresol | 0.2 | 0.2 | 0.2 | 0.2 | 0.2 |
| Toluene-2,5-diamine | 0.1 | 0.1 | 0.1 | 0.1 | 0.1 |
| Aqueous ammonia (28% by mass) | 6.0 | 6.0 | 6.0 | 6.0 | 6.0 |
| Ammonium hydrogen carbonate | 10.0 | 10.0 | 10.0 | 10.0 | 10.0 |
| Decylglucoside | 8.5 | 5.1 | 18.7 | 8.5 | 8.5 |
| Propylene glycol | 4.0 | 4.0 | 4.0 | 4.0 | 4.0 |
| EDTA-4Na | 0.1 | 0.1 | 0.1 | 0.1 | 0.1 |
| Ascorbic acid | 0.4 | 0.4 | 0.4 | 0.4 | 0.4 |
| Anhydrous sodium sulfite | 0.5 | 0.5 | 0.5 | 0.5 | 0.5 |
| Water | Balance | Balance | Balance | Balance | Balance |
| Second part | | | | | |
| Aqueous hydrogen peroxide (35% by mass) | 16.3 | 16.3 | 16.3 | 16.3 | 16.3 |
| Sodium laureth sulfate | 1.0 | 0.6 | 2.2 | 1.0 | 1.0 |
| Cetanol | 0.6 | 0.6 | 0.6 | 0.2 | 1.5 |
| Oxyquinoline sulfate | 0.03 | 0.03 | 0.03 | 0.03 | 0.03 |
| Etidronic acid | 0.08 | 0.08 | 0.08 | 0.08 | 0.08 |
| Sodium hydroxide | * | * | * | * | * |
| Water | Balance | Balance | Balance | Balance | Balance |

* Amount required to adjust second part to pH 3.5

TABLE 4

| (% by mass) | Example | | |
|---|---|---|---|
| | 8 | 9 | 10 |
| First part | | | |
| Para-aminophenol | 0.15 | 0.15 | 0.15 |
| Para-amino-ortho-cresol | 0.2 | 0.2 | 0.2 |
| Toluene-2,5-diamine | 0.1 | 0.1 | 0.1 |
| Aqueous ammonia (28% by mass) | 6.0 | 6.0 | 6.0 |
| Ammonium hydrogen carbonate | 10.0 | 10.0 | 10.0 |
| Decylglucoside | 6.0 | 6.0 | 9.0 |
| Laureth-23 | 2.0 | 2.0 | 3.0 |
| Propylene glycol | 5.0 | 5.0 | 4.0 |
| Polyquaternium-7 | 0.5 | 0.5 | 0.5 |
| EDTA-4Na | 0.1 | 0.1 | 0.1 |
| Ascorbic acid | 0.4 | 0.4 | 0.4 |
| Anhydrous sodium sulfite | 0.5 | 0.5 | 0.5 |
| Fragrance | 0.5 | 0.5 | 0.5 |
| Water | Balance | Balance | Balance |
| Second part | | | |
| Aqueous hydrogen peroxide (35% by mass) | 16.3 | 16.3 | 16.3 |
| Sodium laureth sulfate | 2.0 | 3.0 | 4.0 |
| Lauric acid | 0.01 | 0.01 | 0.01 |
| Glycerine | 0 | 2.0 | 0 |
| Etidronic acid | 0.08 | 0.08 | 0.08 |
| Sodium hydroxide | * | * | * |
| Water | Balance | Balance | Balance |

* Amount required to adjust second part to pH 3.5

TABLE 5

| (% by mass) | Example | |
|---|---|---|
| | 11 | 12 |
| First part | | |
| Toluene-2,5-diamine | 0.3 | 0.3 |
| Meta-aminophenol | 0.25 | 0.25 |
| 2,4-Diaminophenoxyethanol hydrochloride | 0.05 | 0.05 |
| Aqueous ammonia (28% by mass) | 5.0 | 5.0 |
| Ammonium hydrogen carbonate | 10.0 | 10.0 |
| Decylglucoside | 6.0 | 8.0 |
| Laureth-23 | 2.0 | 2.5 |
| Propylene glycol | 4.0 | 3.5 |
| Ethanol | 7.0 | 7.0 |
| Polyquaternium-7 | 0.6 | 0.6 |
| Polyquaternium-22 | 0.4 | 0.4 |
| EDTA-4Na | 0.1 | 0.1 |
| Ascorbic acid | 0.4 | 0.4 |
| Anhydrous sodium sulfite | 0.5 | 0.5 |
| Fragrance | 0.5 | 0.5 |
| Water | Balance | Balance |
| Second part | | |
| Aqueous hydrogen peroxide (35% by mass) | 16.3 | 16.3 |
| Sodium laureth sulfate | 0.8 | 1.8 |
| Lauramide propyl betaine | 0.03 | 0.08 |
| Lauryl hydroxysultaine | 0.02 | 0.08 |
| Octoxyglycerine | 0.05 | 0.05 |
| Cetanol | 0.5 | 0.5 |
| Stearyl alcohol | 0.2 | 0.2 |
| Lauric acid | 0.02 | 0.02 |
| Etidronic acid | 0.08 | 0.08 |
| Sodium hydroxide | * | * |
| Water | Balance | Balance |

* Amount required to adjust second part to pH 3.5

TABLE 6

| (% by mass) | Example | | |
|---|---|---|---|
| | 13 | 14 | 15 |
| First part | | | |
| Toluene-2,5-diamine | 1.6 | 1.6 | 1.6 |
| Meta-aminophenol | 0.2 | 0.2 | 0.2 |
| Resorcin | 1.0 | 1.0 | 1.0 |
| 2,4-Diaminophenoxyethanol hydrochloride | 0.5 | 0.5 | 0.5 |
| Aqueous ammonia (28% by mass) | 3.0 | 3.0 | 3.0 |
| Ammonium hydrogen carbonate | 2.5 | 2.5 | 2.5 |
| Decylglucoside | 8.0 | 8.0 | 8.0 |
| Trideceth-9 | 1.0 | 1.0 | 1.0 |
| Laureth-23 | 2.0 | 2.0 | 2.0 |
| Sodium laureth sulfate | 1.5 | 1.5 | 1.5 |
| Lauramide propyl betaine | 0.01 | 0.01 | 0.35 |
| Myristyl alcohol | 0.1 | 0.1 | 0.1 |
| Propylene glycol | 1.0 | 2.0 | 10.0 |
| Ethanol | 10.0 | 10.0 | 5.0 |
| Polyquaternium-7 | 0.6 | 0.6 | 0.6 |
| Polyquaternium-22 | 0.4 | 0.4 | 0.4 |
| EDTA-4Na | 0.1 | 0.1 | 0.1 |
| Ascorbic acid | 0.3 | 0.3 | 0.3 |
| Anhydrous sodium sulfite | 0.4 | 0.4 | 0.4 |
| Fragrance | 0.5 | 0.5 | 0.5 |
| Water | Balance | Balance | Balance |
| Second part (common) | | | |
| Aqueous hydrogen peroxide (35% by mass) | 16.3 | 16.3 | 16.3 |
| Sodium laureth sulfate | 2.5 | 2.5 | 0.4 |
| Octoxyglycerine | 0.1 | 0.1 | 0.1 |
| Lauryl hydroxysultaine | 0.01 | 0.01 | 0.1 |
| Cetanol | 0.35 | 0.35 | 0.35 |

TABLE 6-continued

| (% by mass) | Example 13 | Example 14 | Example 15 |
|---|---|---|---|
| Stearyl alcohol | 0.15 | 0.15 | 0.15 |
| Oxyquinoline sulfate | 0.04 | 0.04 | 0.04 |
| Etidronic acid | 0.08 | 0.08 | 0.08 |
| Sodium hydroxide | * | * | * |
| Water | Balance | Balance | Balance |

* Amount required to adjust second part to pH 3.5

"Hair Dyeing Procedure"

1) Whole Head Hair Dyeing

Each stock solution and a propellant are filled in an aerosol container. Then, the container is sufficiently shaken, and the contents are discharged after confirmation that the stock solution and the propellant are uniformly mixed. Both the obtained foams of the first part and the second part are placed at the same time on one gloved hand and immediately applied to a head hair. The placement of the contents discharged from the aerosol containers in the hand and application to the head hair are repeated to apply the whole hair dye in the aerosol containers to the head hair.

Immediately after completion of application, the mixture of the applied foams of the first part and the second part is re-foamed by rubbing the whole head hair with the fingers of both gloved hands for 20 seconds.

Then, the foams are left for 10 minutes.

Then, the re-foam operation is performed again for 30 seconds.

Then, the foams are left until 30 minutes passes after completion of application of the hair dye.

The whole head hair is rinsed with warm water for washout of the applied hair dye, shampooed two times, treated once with a conditioner, and dried after washout of the conditioner.

2) Partial Hair Dyeing

Partial hair dyeing procedures are performed in the same way as in the above-mentioned whole head hair dyeing except that the hair dye is "applied to a specific portion" such as only the hair in the back of the head, the "hair dye used is applied in a necessary amount according to the area to be dyed", and "after completion of application, the specific portion in the head hair is rubbed for re-foam."

The invention claimed is:

1. A head hair dyeing method using a two-part hair dye composition which comprises: a first part comprising a first part stock solution and a propellant, the first part stock solution comprising an alkali agent and a surfactant; a second part comprising a second part stock solution and a propellant, the second part stock solution comprising hydrogen peroxide and a surfactant; and two aerosol containers for respectively discharging the first part and the second part as foam, the method comprising respectively discharging the first part and the second part as foam from the containers, applying the foam mixture to the head hair, and then re-foaming the mixture on the head hair.

2. The head hair dyeing method according to claim 1, wherein the foam applied to the head hair is foamed with fingers.

3. The head hair dyeing method according to claim 1 or 2, wherein the foam is applied to the whole head hair and re-foamed.

4. The head hair dyeing method according to claim 1 or 2, wherein the foam is applied to a part of the head hair and re-foamed.

* * * * *